United States Patent

Manoury et al.

Patent Number: 5,530,002
Date of Patent: Jun. 25, 1996

[54] 1-[2-(1H-INDEN-3-YL)ETHYL]-4-(NAPHTH-1-YL)PIPERAZINE DERIVATIVES, THEIR PREPARATION AND THEIR APPLICATION IN THERAPEUTICS

[75] Inventors: Phillip Manoury, Verrieres le Buisson; Daniel Obitz, Antony; Michel Peynot, L'Hay les Roses; Mireille Sevrin, Paris; Pascal George, Saint Arnoult en Yvelines, all of France

[73] Assignee: Synthelabo, Le Plessis Robinson, France

[21] Appl. No.: 385,927

[22] Filed: Feb. 9, 1995

[30] Foreign Application Priority Data

Feb. 16, 1994 [FR] France .................... 94 01736

[51] Int. Cl.$^6$ ............... C07D 295/033; C07D 295/096; A61K 31/495
[52] U.S. Cl. ............ 514/255; 544/392; 544/394; 564/222; 564/428
[58] Field of Search ................. 544/392, 394; 514/255

[56] References Cited

U.S. PATENT DOCUMENTS

| | | | |
|---|---|---|---|
| 4,130,646 | 12/1978 | Vogt et al. | 424/250 |
| 4,845,221 | 7/1989 | Stack et al. | 544/392 |
| 5,194,437 | 3/1993 | Peglion et al. | 514/254 |

FOREIGN PATENT DOCUMENTS

94/00441   1/1994   WIPO .

OTHER PUBLICATIONS

Renth et al, *Chemical Abstracts*, vol. 76, No. 113247 (1972).

*Primary Examiner*—Emily Bernhardt
*Attorney, Agent, or Firm*—Foley & Lardner

[57] ABSTRACT

Compounds of formula:

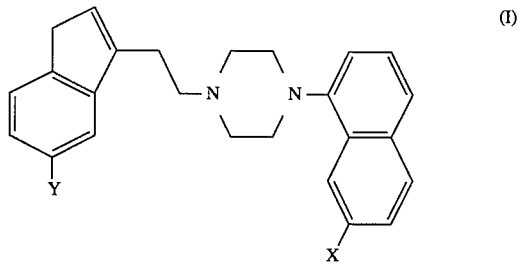

in which X represents a hydrogen atom, a $C_1$–$C_3$ alkoxy group or a cyclopropylmethoxy group and Y represents a hydrogen atom or a methoxy group, are useful in the therapy of conditions.

4 Claims, No Drawings

1-[2-(1H-INDEN-3-YL)ETHYL]-4-(NAPHTH-1-YL)PIPERAZINE DERIVATIVES, THEIR PREPARATION AND THEIR APPLICATION IN THERAPEUTICS

The present invention relates to 1-[2-(1H-inden-3-yl)ethyl]-4-(naphth-1-yl)piperazine derivatives, their preparation and their application in therapeutics.

The compounds of the invention have the formula:

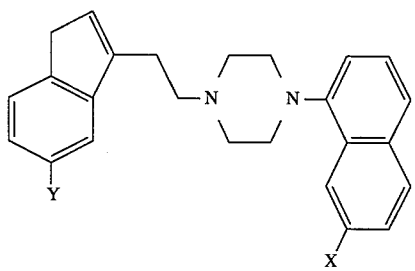

in which
X represents a hydrogen atom, a $C_1$–$C_3$ alkoxy group or a cyclopropylmethoxy group, and
Y represents a hydrogen atom or a methoxy group.

X preferably represents a $C_1$–$C_3$ alkoxy group, especially a methoxy group, and Y preferably represents a methoxy group.

The compounds of the invention may exist as free bases and as addition salts, especially with pharmaceutically acceptable acids.

Compounds whose chemical structure is similar to that of the compounds of formula (I), and which can be used as antidepressant and anxiolytic agents, are described in European Patent Application EP-A-0490772.

In accordance with a feature of the invention, the compounds of formula (I) are prepared by the processes illustrated in schemes 1 and 2 below.

Scheme 1

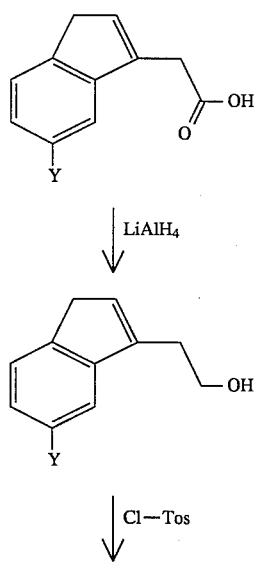

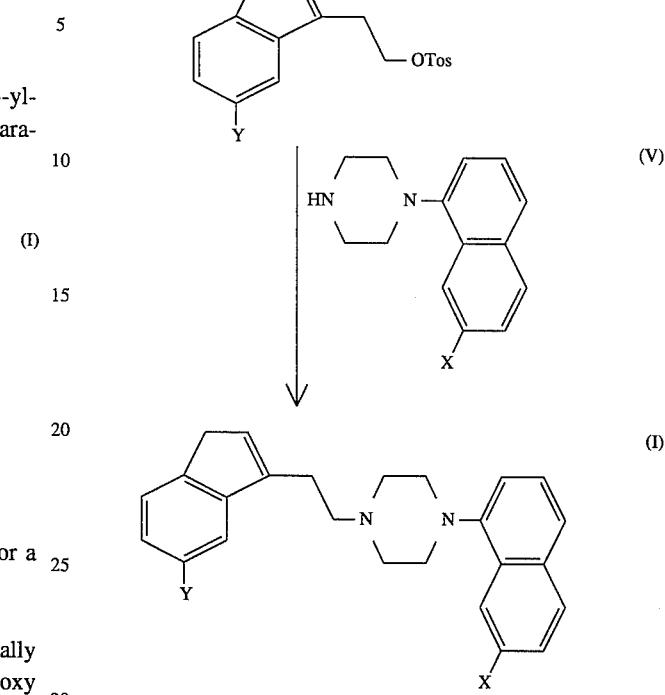

In the process of scheme 1, a 1H-indene-3-acetic acid derivative of formula (II) (in which Y is as defined above) is treated with a simple or complex reducing agent such as an alkali metal hydride or metal hydride, for example lithiumaluminium hydride, boron hydride, the boron hydride/tetrahydrofuran complex, the boron hydride/dimethyl sulphide complex, or aluminium hydride, in an inert aromatic or ether solvent, for example toluene, xylene, diethyl ether, tetrahydrofuran or dioxane, at a temperature of from 30° to 140° C., depending on the solvent, to form the alcohol of formula (III). This alcohol is subsequently treated with 4-methylbenzenesulphonyl chloride in the presence of an organic base such as triethylamine or pyridine and, optionally, in the presence of an inert solvent, at a temperature of from 0° to 40° C. in order to obtain the derivative of formula (IV).

Finally, this compound is reacted with a piperazine derivative of formula (V) (in which X is as defined above) at a temperature of from 100° to 150° C., preferably at 130° C., optionally in a high-boiling solvent such as toluene, xylene, N,N-dimethyl-formamide or 1-methylpyrrolidin-2-one.

Scheme 2

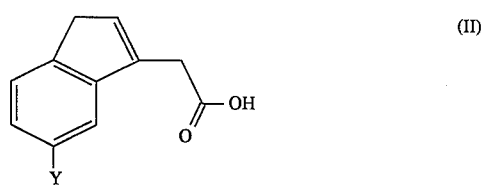

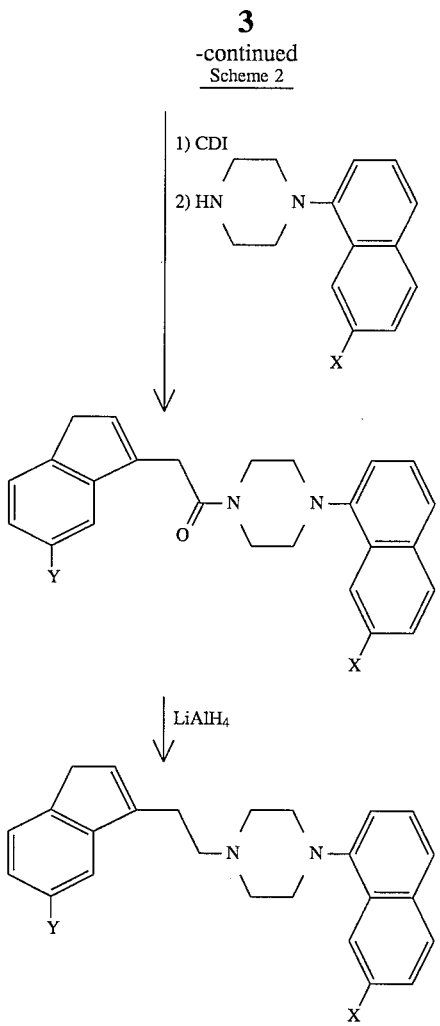

In the process shown in scheme 2, the 1H-indene-3-acetic acid derivative of formula (II) (in which Y is as defined above) is first reacted with N,N'-carbonyldiimidazole (CDI) in an inert solvent such as tetrahydrofuran at a temperature of from 20° to 50° C., in order to obtain in situ the corresponding imidazolide, which is then treated with a piperazine derivative of formula (V) (in which X is as defined above), in an inert solvent such as an ether solvent, for example tetrahydrofuran or dioxane, at a temperature of from 20° to 50° C. in order to obtain the amide of formula (VI). Finally, the latter is reduced by means of a simple or complex reducing agent such as an alkali metal hydride or metal hydride, for example lithium aluminium hydride, boron hydride, the boron hydride/tetrahydrofuran complex, the boron hydride/dimethyl sulphide complex, or aluminum hydride, in an inert, aromatic or ether solvent, for example toluene, xylene, diethyl ether, tetrahydrofuran or dioxane, at a temperature of from 30° to 140° C., depending on the solvent.

The starting materials of formula (II) are described in C.A. 76(23) 140279s, C.A. 104(1) 5652q and J. Chem. Soc. Perkin Trans. (1972) 1(7) 941. 2,3-Dihydro-1H-inden-1-one (Y=H, commercially available) or 6-methoxy-2,3-dihydro-1H-inden-1-one (Y=OCH₃, described in J. Org. Chem. (1970) 35(3) 647 and J. Org. Chem. (1977) 42(12) 2155) is treated with ethyl bromoacetate in the presence of zinc powder under the conditions of the Reformatsky reaction to obtain a mixture of ethyl (6-Y-2,3-dihydro-1H-inden-1-ylidene)acetate and ethyl 5-Y-1H-indene-3-acetate. Hydrolysis of this mixture in a basic alcoholic medium gives the acid of formula (II).

The piperazine derivatives of formula (V) are known and can be obtained by methods described in the literature, for example in the European Patent Applications EP-A-0343050, EP-A-0354093 and EP-A-0434561, in J. Med. Chem. (1986) 29(11) 2379, J. Med. Chem. (1988) 31(10) 1968 and in J. Med. Chem. (1991) 34(8) 2623.

The following Examples illustrate in detail the preparation of compounds according to the invention. The elemental microanalyses and the IR and NMR spectra confirm the structures of the products obtained. The numbers given in brackets in the titles of the Examples correspond to those of the first column of the Table which is given subsequently.

EXAMPLE 1 (COMPOUND NO. 4)

4-[2-(5-Methoxy-1H-inden-3-yl)ethyl]-1-(7-methoxynaphth-1-yl)piperazine (E)-2-butenedioate (1:2)
1.1.5-Methoxy-1H-indene-3-ethanol A suspension is prepared from 0.76 g (0.02 mol) of lithium aluminium hydride in 50 ml of diethyl ether. A solution of 2.04 g (0.01 mol) of 5-methoxy-1H-indene-3-acetic acid is added, and the mixture is stirred and heated at reflux for 32 h. The mixture is cooled, hydrolysed with 1.6 ml of 10% aqueous sodium potassium tartrate solution, heated at boiling for 1 h and filtered. The residue is rinsed with tetrahydrofuran, and the filtrate is evaporated under reduced pressure. 1.8 g of an oily residue are obtained which is purified by distillation. 1.55 g of a yellow liquid are obtained which is used as it is in the following step.

1.2.2-(5-Methoxy-1H-inden-3-yl)ethyl 4-methylbenzenesulphonate 1.27 g (0.0067 mol) of 5-methoxy-1H-indene-3-ethanol are dissolved in 11 ml of dry pyridine. The mixture is stirred and cooled using an ice bath, and 1.4 g (0.0073 mol) of 4-methylbenzenesulphonyl chloride are added in portions. Stirring is continued under cold conditions overnight and then at room temperature for 4 h. The solution obtained is poured into a mixture of 16 ml of 10N hydrochloric acid and 48 g of ice. The mixture obtained is treated with diethyl ether, and the organic phase is separated, washed with water, dried over magnesium sulphate and filtered. The filtrate is evaporated under reduced pressure. 1.94 g of a colourless oily product are obtained which is used as it is in the following step.

1.3. 4-[2-(5-Methoxy-1H-inden-3-yl)ethyl]-1-(7-methoxynaphth-1-yl)piperazine (E)-2-butenedioate (1:2)

2.07 g (0.006 mol) of 2-(5-methoxy-1H-inden-3-yl)ethyl 4-methylbenzenesulphonate and 2.90 g (0.012 mol) of 1-(7-methoxynaphth-1-yl)piperazine are mixed, and the mixture is stirred, placed under an argon atmosphere and heated in an oil bath at 130° C. for 2 h. The mixture is then taken up in dichloromethane and the solution is washed with water, with dilute sodiumhydroxide solution and then again with water, dried over magnesium sulphate and filtered. The filtrate is evaporated under reduced pressure. 4.08 g of an oil are obtained which is purified by chromatography on a column of silica gel, eluting with a 92:8 mixture of dichloromethane/acetone. 2.09 g of a base are obtained. 2.03 g (0.0049 mol) of this base are dissolved in a mixture of 2-propanol and diethyl ether. The solution is warmed and a solution of 0.569 g of fumaric acid in hot 2-propanol is added. The mixture is cooled while stirring and left to stand overnight. 2.16 g of neutral fumarate are obtained. Melting point: 158°–159° C.

EXAMPLE 2 (COMPOUND NO. 2)

4-[2-(5-Methoxy-1H-inden-3-yl)ethyl]-1-(naphth-1-yl)piperazine 2.1. 4-[(5-Methoxy-1H-inden-3-yl)acetyl]-1-(naphth-1-yl)piperazine 2.0 g (0.012 mol) of N,N'-carbonyldiimidazole are added in small portions to a solution of 2.45 g (0.012 mol) of 5-methoxy-1H-indene-3-acetic acid in 12 ml of tetrahydrofuran, which has been placed under an argon atmosphere, and the mixture is stirred for 1 h. A solution of 2.55 g (0.012 mol) of 1-(naphth-1-yl)piperazine in 10 ml of tetrahydrofuran is added, and the mixture is left to stand overnight. The solvent is evaporated under reduced pressure. The residual oil is taken up in water and diethyl ether, and the solid obtained is collected by filtration and dried. 4.13 g of a product are obtained which is used as it is in the following step.

2.2. 4-[2-(5-Methoxy-1H-inden-3-yl)ethyl]-1-(naphth-1-yl)piperazine 0.76 g (0.02 mol) of lithium aluminum hydride are placed under an argon atmosphere in a 500 ml round-bottomed flask and covered with diethyl ether. A Soxhlet extractor containing 2.0 g (0.005 mol) of 4-[(5-methoxy-1H-inden-3-yl)acetyl]-1-(naphth-1-yl)piperazine is placed on top of the flask, and the mixture is reacted with refluxing of the ether for 30 h. The reaction mixture is treated with 1.6 ml of 10% aqueous sodium potassium tartrate solution and filtered. The solid is washed with diethyl ether and then with tetrahydrofuran, and the filtrate is evaporated under reduced pressure.

An oil is obtained which crystallizes. After treatment with diethyl ether and recrystallization from a mixture of hexane and diisopropyl ether, 0.45 g of a compound are finally obtained. Melting point: 102°–103° C.

EXAMPLE 3 (COMPOUND NO. 3)

4-[2-(1H-Inden-3-yl)ethyl]-1-(7-methoxynaphth-1-yl)piperazine (E)-2-butenedioate (1:1)

3.1. 1H-Indene-3-ethanol

A suspension is prepared from 3.4 g (0.09 mol) of lithium aluminium hydride in 200 ml of dry diethyl ether. A solution of 7.7 g (0.044 mol) of 1H-indene-3-acetic acid in 150 ml of diethyl ether is added dropwise, and the mixture is stirred and heated at reflux for 20 h. The mixture is cooled, hydrolysed with approximately 8 ml of 10% aqueous sodium potassium tartrate solution, heated at boiling for 1 h and filtered. The residue is rinsed with diethyl ether, and the filtrate is evaporated under reduced pressure. The residue is purified by distillation. 5.2 g of a product are obtained which is used as it is in the following step.

3.2. 2-(1H-Inden-3-yl)ethyl 4-methylbenzenesulphonate 5 g (0.031 mol) of 1H-indene-3-ethanol are dissolved in 50 ml of dry pyridine. The mixture is stirred and cooled using an ice bath, 5.9 g (0.031 mol) of 4-methylbenzenesulphonyl chloride are added in portions, and stirring is continued under cold conditions for 1 h and then at room temperature for 4 h. The solution obtained is poured into a mixture of 100 ml of 10N hydrochloric acid and 200 g of ice. The mixture is extracted twice with diethyl ether, and the organic phase is separated, washed with water, dried over magnesium sulphate and filtered. The filtrate is evaporated under reduced pressure. 7 g of an oily product are obtained which is used as it is in the following step.

3.3. 4-[2-(1H-Inden-3-yl)ethyl]-1-(7-methoxynaphth-1-yl)piperazine (E)-2-butenedioate (1:1)

1.15 g (0.00366 mol) of 2-(1H-inden-3-yl)ethyl 4-methylbenzenesulphonate and 1.95 g (0.008 mol) of 1-(7-methoxynaphth-1-yl)piperazine are mixed, and the mixture is stirred, placed under an argon atmosphere and heated in an oil bath at 130° C. for 3 h. The mixture is then cooled, taken up in 10 ml of 10% :sodium hydroxide solution and extracted with dichloromethane. The extract obtained is washed with water, dried over magnesium sulphate and filtered, and the filtrate is evaporated under reduced pressure. The residue is purified by chromatography on a column of silica gel, eluting with a 98:2 mixture of dichloromethane/acetone. 1.3 g (0.00338 mol) of a base are obtained which is dissolved in 50 ml of 2-propanol. 0.4 g of fumaric acid are added, and the mixture is cooled with stirring, left to stand overnight, and filtered. The residue is washed with diethyl ether, dried and recrystallized from ethanol. 1.15 g of fumarate are finally obtained. Melting point: 184°–185° C.

EXAMPLE 4 (COMPOUND NO. 10)

4-[2-(5-Methoxy-1H-inden-3-yl ethyl]-1-[7-(cyclopropylmethoxy)naphth-1-yl]piperazine (E) -2-butenedioate (1:1)

4.1. N-(7-Hydroxynaphth-1-yl)acetamide 100 g (0.55 mol) of 8-aminonaphth-2-ol are poured into 125 ml (135.25 g or 1.325 mol) of acetic anhydride cooled in an ice bath, and the mixture is stirred under cold conditions for 1 h. The mixture obtained is poured into 375 ml of ice-water and stirred for several hours. The violet solid is collected by filtration, washed three times with 30 ml of diethyl ether and dried under reduced pressure. 108.8 g of a product melting point: 193°–195° C. are obtained which is used as it is in the following step.

4.2. N-[7-(Cyclopropylmethoxy)naphth-1-yl]acetamide 17.1 g (0.085 mol) of N-(7-hydroxynaphth-1-yl)acetamide in solution in 50 ml of dimethyl sulphoxide are added under a nitrogen atmosphere to a suspension of 3.4 g (0.085 mol) of sodium hydride in oil, washed beforehand with dry pentane), in 100 ml of dimethyl sulphoxide, while the mixture is cooled with an ice-water bath. Stirring is continued at room temperature for 2 h. 9.05 g (0.1 mol) of (chloromethyl)cyclopropane are added, and the mixture is stirred at room temperature for 4 h and left to stand overnight. The mixture is poured into 1 l of water, stirred for 1 h and left to stand overnight under cold conditions. The solid is separated by filtration, washed with water and dried. 13 g of a product melting point: 154°–155° C., are obtained which is used as it is in the following step.

4.3. 7-(Cyclopropylmethoxy)naphthalene-1-amine

A mixture of 13 g (0.05 mol) of N-[7-(cyclopropylmethoxy)naphth-1-yl]acetamide, 35 ml of 10N sodium hydroxide solution and 150 ml of 2-methoxyethanol is heated at reflux for 4 h under a nitrogen atmosphere. The solvent is evaporated under reduced pressure. The residue is taken up in 200 ml of dichloromethane and 200 ml of water, and the mixture is stirred in the presence of carbon black and filtered over kieselguhr. The organic phase obtained is separated, dried over magnesium sulphate and filtered. The solvent is evaporated under reduced pressure and the residue is purified by chromatography on a column of silica gel, eluting with dichloromethane. 7.8 g of an oil are obtained which crystallizes on cooling to give a product, melting point: 49°–50° C.

4.4. 1-[7-(Cyclopropylmethoxy)naphth-1-yl]piperazine

A mixture of 7.7 g (0.036 mol) of 7-(cyclopropylmethoxy)naphthalene-1-amine, 6 g (0.036 mol) of bis(2-chloroethyl)amine hydrochloride, 50 ml of butanol and approximately 50 mg of potassium iodide is heated at reflux for 10 h under a nitrogen atmosphere. 2.5 g (0.018 mol) of potassium carbonate are added and heating at reflux is continued for 10 h, and then, twice, a further 1.25 g (0.009 mol) of potassium carbonate are added and the mixture is heated at reflux for 10 h. The butanol is evaporated. The residue is taken up in 100 ml of dichloromethane and 50 ml of 10% sodium hydroxide solution. The mixture is stirred in the presence of carbon black and filtered. The organic phase is separated and dried over magnesium sulphate. The solvent is evaporated under reduced pressure and the residue is purified by chromatography on a column of silica gel, eluting with a 90:10 mixture of dichloromethane/methanol. After evaporation of the solvent, 4.2 g of an oily product are obtained which is used as it is in the following step.

4.5. 4-[2-(5-Methoxy-1H-inden-3-yl)ethyl]-1-[7-(cyclopropylmethoxy)naphth-1-yl]piperazine (E)-2-butenedioate (1:1)

A mixture of 1.14 g (0.0033 mol) of 2-(5-methoxy-1H-inden-3-yl)ethyl 4-methylbenzenesulphonate and 2 g (0.007 mol) of 1-[7-cyclopropylmethoxy)naphth-1-yl]piperazine is heated slowly under a nitrogen atmosphere, and heating is maintained at 130° C. for 3 h. The mixture is taken up in 20 ml of 10% sodium hydroxide solution and extracted with dichloromethane. The organic phase is dried over magnesium sulphate. The solvent is evaporated under reduced pressure and the residue is purified by chromatography on a column of silica gel, eluting with a 98:2 mixture of dichloromethane/acetone. 1.3 g (0.00286 mol) of a base are obtained which is dissolved in 20 ml of 2-propanol. The solution is heated at reflux and 0.33 g (0.00286 mol) of fumaric acid are added. The mixture is allotted to cool. The solid is separated by filtration, recrystallized from ethanol, washed with diethyl ether and dried. 0.65 g of fumarate, melting point: 154°–155° C., is isolated.

The following Table illustrates the chemical structures and the physical properties of some compounds of formula I according to the invention. In the column "X", "OCH$_2$cC$_3$H$_5$" denotes a cyclopropylmethoxy group. In the column "Salt", "-" denotes a compound in the form of a base, "fum." denotes a fumarate or (E)-2-butenedioate; the ratio indicated in brackets is the molar ratio of acid:base.

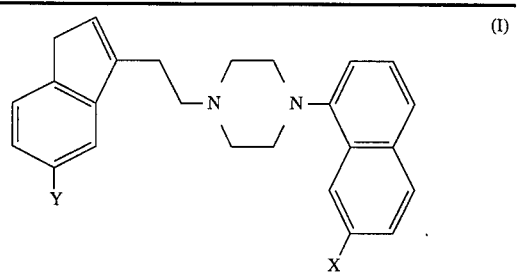

(I)

| Compound No. | X | Y | Salt | m.p. (°C.) |
|---|---|---|---|---|
| 1 | H | H | fum. (1:1) | 224–225 |
| 2 | H | OCH$_3$ | — | 102–103 |
| 3 | OCH$_3$ | H | fum. (1:1) | 184–185 |
| 4 | OCH$_3$ | OCH$_3$ | fum. (1:2) | 158–159 |
| 5 | OCH$_2$CH$_3$ | H | fum. (1:1) | 183–184 |
| 6 | OCH$_2$CH$_3$ | OCH$_3$ | fum. (1:1) | 142–143 |
| 7 | OCH$_2$CH$_2$CH$_3$ | OCH$_3$ | fum. (1:1) | 163–164 |
| 8 | OCH(CH$_3$)$_2$ | OCH$_3$ | fum. (1:1) | 200–201 |
| 9 | OCH$_2$cC$_3$H$_5$ | H | fum. (1:1) | 205–206 |
| 10 | OCH$_2$cC$_3$H$_5$ | OCH$_3$ | fum. (1:1) | 154–155 |

The compounds of the invention have been subjected to tests which have demonstrated their advantage as therapeutic substances.

For this purpose they have been tested in vitro for their affinity for serotoninergic receptors of the 5-HT$_{1A}$ type, which are present in the rat hippocampus, in accordance with a protocol described by Sanger and Schoemaker, *Psychopharmacology* (1992) 108 85–92. The compounds displace the binding to the 5-HT$_{1A}$ receptors of a specific labelled ligand, [$^3$H]-8-hydroxy-2-(di-n-propylamino)tetralin (denoted hereinafter "[$^3$H]-8-OH-DPAT" and described by Gozlan et al., *Nature* (1983) 305 140–142).

The animals used are male Sprague-Dawley rats weighing 160 to 200 g each. They are decapitated, their brains are removed and the hippocampus is excised. The tissue is ground in an Ultra-Turrax Polytron™ apparatus for 30 s at half the maximum speed in 10 volumes of 50 mM Tris buffer whose pH has been adjusted to 7.4 with hydrochloric acid (equivalent to 100 mg of fresh tissue per ml). The homogenized tissues are washed three times at 4° C., centrifuging them each time for 10 min at 48,000 g and resuspending the pellet in fresh, cooled buffer. Finally, the last pellet is suspended in the buffer to arrive at a concentration of 100 mg of original tissue per ml of 50 mM buffer. The suspension is then incubated at 37° C. for 10 min.

Binding with [$^3$H]-8-OH-DPAT (1 nM) is determined by incubating 100 µl of membrane suspension in a final volume of 1 ml of buffer containing 10 µM of pargyline and 3 µM of paroxetine.

After incubation at 37° C. for 15 min the membranes are recovered by filtration on Whatman GF/B™ filters which are washed three times with aliquot quantities of 5 ml of ice-cold buffer. The filters are extracted with the scintillation liquid and their radioactivity is measured by liquid scintigraphy. The specific binding of the [$^3$H]-8-OH-DPAT is defined as the radioactive quantity retained on the filters which can be inhibited by co-incubation in 5-hydroxytryptamine at a concentration of 10 µM. At a concentration of 1 nM of [$^3$H]-8-OH-DPAT, the specific binding represents 90% of the total radioactivity recovered on the filter.

For each concentration of compound which was studied, the percentage inhibition of binding with [$^3$H]-8-OH-DPAT is determined, followed by the concentration IC$_{50}$, which is the concentration which inhibits the binding by 50%. The IC$_{50}$ values are between 10 and 300 nM.

The compounds of the invention were also subjected to an in vitro study of their affinity for the serotoninergic 5HT$_{1D}$ receptors present in bovine caudate nucleus, which is demonstrated by the displacement of a specific labelled ligand, [$^3$H]-5-hydroxytryptamine, essentially as described by Heuring and Peroutka in *J. Neurosci.,* (1987), 7, 804–903.

Bovine caudate nucleus (Collectorgane, Paris) is stored at −80° C. until it is used. The tissue is ground in an Ultra-Turrax Polytron™ apparatus for 30 s at half the maximum speed in 10 volumes of 50 mM Tris buffer whose pH is adjusted to 7.4 with hydrochloric acid (equivalent to 100 mg of fresh tissue per ml). The homogenized tissues are washed twice at 4° C. and centrifuged for 10 min at 40,000 g, the pellet being resuspended each time in ice-cold buffer. Finally, the last pellet is suspended in the buffer to arrive at a concentration of 100 mg of original tissue per ml of 50 mM buffer, and the suspension is incubated at 37° C. for 15 min. The membrane suspension is subsequently centrifuged for 10 min at 40,000 g and the pellet is resuspended in 8 volumes of incubation medium containing Tris (50 mM), ascorbic acid (0.1%), calcium chloride (4 mM), pargyline (10 µM), mesulergine (100 nM) and 8-hydroxydipropylaminotetraline (100 nM), whose pH is adjusted to 7.4 with hydrochloric acid.

Binding of [³H]-5-hydroxytryptamine (2 nM) is determined by incubating 100 μl of membrane suspension in a final volume of 1 ml of incubation medium. After incubation for 30 min at 37° C., followed by incubation for 5 min at between 0° and 4° C., the membranes are recovered by filtration on Whatman GF/B™ filters which are washed twice with aliquot quantities of 1 ml of ice-cold 50 mM Tris buffer, whose pH is adjusted to 7.4 with hydrochloric acid.

The filters are extracted with the scintillation liquid and the radioactivity is measured by liquid scintigraphy. The specific binding of the [³H]-5-hydroxytryptamine is defined as the quantity of radioactivity retained on the filters which can be inhibited by co-incubation with 5-hydroxytryptamine at 0.1 μM. At a concentration of 2 nM of [³H]-5-hydroxytryptamine, the specific binding represents 70% of the total radioactivity recovered on the filter.

For each concentration of compound studied, the percentage inhibition of binding with [³H]-5-hydroxytryptamine is determined, followed by the concentration $IC_{50}$, the concentration which inhibits the binding by 50%.

The most active compounds of the invention in this test have an $IC_{50}$ of less than 30 nM.

The compounds of the invention were also subjected to an in vitro test of displacement of the binding of spiperone to the serotoninergic receptors (5-$HT_2$) of the rat cerebral cortex. For this test the brains are removed from rats and the cortex is dissected and homogenized at 0° C. in 10 volumes of a mixture containing, per liter, 50 millimol of Tris/HCl buffer, pH=7.4, 120 millimol of sodium chloride and 5 millimol of potassium chloride. The homogenous mixture is centrifuged at 40,000 g for 10 min and then, in a procedure which is carried out twice, the pellet is recovered, washed and suspended in the same buffer mixture, rehomogenized and centrifuged. Finally, the last pellet is diluted in the same buffer mixture in a proportion of 100 mg of wet tissue per ml of buffer. The tissue is then subjected to a preliminary incubation for 10 min at 37° C. in the presence of 10 micromol/l of pargyline, then to incubation for 20 min at 37° C. in the presence of ³H-spiperone (specific activity: 15 to 30 Ci per millimole) at a concentration of 0.3 nanomol/l, and in the presence of the compound to be tested.

The membranes are subsequently recovered by filtration on Whatman GF/B™ filters which are washed twice with 5 ml of cold buffer. The radioactivity retained by the filter is measured by liquid scintigraphy.

In order to evaluate the activity of the compounds, the curve is established of the percentage inhibition of the specific binding of ³H-spiperone as a function of the concentration of displacing drug. The concentration $IC_{50}$, the concentration which inhibits 50% of the specific binding, is determined graphically. The specific binding is defined as being the binding displaced by 100 micromol/l of 5-HT.

The $IC_{50}$ concentrations of the compounds of the invention are between 50 and 1,500 nM.

The compounds of the invention were also subjected to an in vitro study of their affinity for the $5HT_{1C}$ serotoninergic receptors present in the pig choroidal plexus which is demonstrated by the displacement of the binding of a specific labelled ligand, [³H]-mesulergine, essentially as described by Pazos et al., in *Eur. J. Pharmacol.*, (1984), 106, 539–546, and by Yagalof and Hartig in *Mol. Pharmacol.*, (1986), 26, 120–125.

The choroidal plexus (Collectorgane, Paris) is stored at −80° C. until it is used. The tissue is homogenized in a Potter™ homogenizer by 10 to 15 movements (800 rpm) in 10 volumes of sucrose (0.32M) at a temperature of from 0° to 4° C. The membrane suspension is centrifuged for 10 min at 1000 g (4° C.) and the supernatant is centrifuged for 20 min at 30,000 g (4° C.). The pellet is suspended in 10 volumes of 50 mM Tris buffer whose pH is adjusted to 7.4 with hydrochloric acid, and subsequently incubated at 37° C. for 15 min. Finally, the suspension is centrifuged for 20 min at 30,000 g (4° C.) and the pellet is taken up in 28 volumes of incubation buffer containing Tris (50 mM), ascorbic acid (0.1%), calcium chloride (4 mM) and pargyline (10 μM), whose pH is adjusted to 7.4 with hydrochloric acid.

Binding with [³H]-mesulergine (1 nM) is determined by incubating 100 μl of membrane suspension in a final volume of 500 μl of incubation medium.

After incubation for 30 min at 37° C. followed by incubation for 5 min at between 0° and 4° C., the membranes are recovered by filtration on Whatman GF/B™ filters which have been treated beforehand for 30 min with polyethylenimine at a concentration of 0.05%, and the membranes are washed with twice 1 ml of ice-cold 50 mM Tris buffer whose pH is adjusted to 7.4 with hydrochloric acid.

The filters are extracted with the scintillation liquid and the radioactivity is measured by liquid scintigraphy. Specific binding of the [³H]-mesulergine is defined as the quantity of radioactivity retained on the filters which can be inhibited by co-incubation with 5-hydroxytryptamine at a concentration of 10 μM. At a concentration of 1 nM of [³H]-mesulergine, the specific binding represents 90% of the total radioactivity recovered on the filter.

For each concentration of compound which was studied, the percentage inhibition of the binding with [³H]-mesulergine is determined followed by the concentration $IC_{50}$, the concentration which inhibits the binding by 50%.

The compounds of the invention have, in this test, $IC_{50}$ values of from 5 to 500 nM.

In vivo, the central activity (of the $5HT_{1A}$ type) of the compounds of the invention was evaluated by their effects on the "PGO spikes" (ponto-geniculooccipital spikes) induced by reserpine (PGO-R test) in the cat, according to the method described by H. Depoortere, Sleep 1976, 3rd Europ. Congr. Sleep Res., Montpellier 1976, 358–361 (Karger, Basel 1977).

Cumulative doses of the compounds to be studied (from 0.1 to 3 mg/kg, intravenously) are administered at intervals of 30 min, 4 h after intraperitoneal injection of a dose of 0.75 mg/kg of reserpine, to curarized cats under artificial ventilation. The electroencephalographic and phase activities (PGO-R spikes) are picked up with the aid of cortical and deep electrodes (lateral geniculum).

For each dose of compound studied, the percentage reduction in the number of PGO spikes is determined followed by the $AD_{50}$, the active dose which reduces this number of spikes by 50%.

For the compounds of the invention, the $AD_{50}$ values are lower than 0.3 mg/kg given intravenously.

Finally, the antiserotoninergic activity (of the $5HT_2$ type) of the compounds of the invention was studied by their effect on the inhibition of head twitches caused by L-5-hydroxytryptophan (L-5-HTP) in mice, according to the method described by Corne et al., *Br. J. Pharmacol.* (1962) 20 106–120.

Male CD1 mice (Charles River France, 18 to 22 g in body weight) receive the products to be studied at increasing doses, or the solvent, intraperitoneally or orally, simultaneously with (i.p.) or sixty minutes before (p.o.) a subcutaneous injection of L-5-HTP at a dose of 250 mg/kg. Forty-five minutes after this injection of 5-HTP, the number of twitches is counted for each mouse for one minute.

For each treatment a calculation is made of the average number of twitches and the percentage variation relative to the control batch.

On the basis of the dose-effect curve, the $AD_{50}$ (active dose 50%, or the dose which reduces by 50% the average number of twitches relative to the control animals) is determined by the graphical method of Miller and Tainter (*Proc. Soc. Exp. Biol. Med.* (1944) 57 261).

The $AD_{50}$ values for the compounds of the invention are less than 3 mg/kg intraperitoneally and are of the order of 1.5 mg/kg orally.

The results of the tests show that the compounds of the invention have a strong affinity for serotoninergic receptors of types $5HT_{1A}$, $5HT_{1D}$ and $5HT_{1C}$ as well as a certain degree of affinity for the $5HT_2$ receptors. In vivo they possess $5HT_{1A}$ agonist and $5HT_2$ antagonist properties.

These results suggest that the compounds can be used for the treatment of all conditions which are linked to dysfunction of the serotoninergic receptors of type $5HT_{1A}$, $5HT_{1D}$, $5HT_{1C}$ and/or $5HT_2$, in particular for the treatment of states of anxiety, depression, sleep disorders, phobias, obsessive-compulsive disorders, disorders linked to alcoholism, disorders of sexual behaviour, to regulate feeding, and also for the treatment of vascular or cardiovascular disorders such as migraine and hypertension.

For this purpose they may be presented in any pharmaceutical forms which are suitable for enteral or parenteral administration, in combination with apppropriate excipients, for example in the form of tablets, coated tablets, gelatin capsules, other capsules, suppositories, drinkable or injectable solutions or suspensions, whose dosage is such that it allows a daily administration of from 1 to 1000 mg of active substance.

We claim:

1. A compound of the formula:

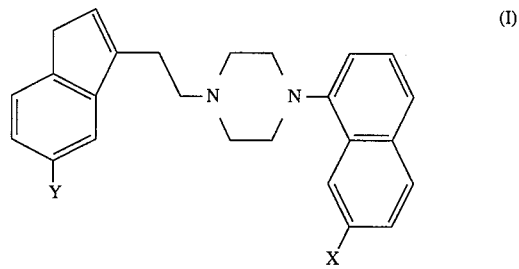

in which

X represents a hydrogen atom, a $C_1$–$C_3$ alkoxy group or a cyclopropylmethoxy group, and Y represents a hydrogen atom or a methoxy group, in the form of the free base or an addition salt thereof.

2. A compound according to claim 1, wherein X represents a $C_1$–$C_3$ alkoxy group and Y represents a methoxy group.

3. A compound according to claim 2, wherein X represents a methoxy group.

4. Pharmaceutical composition, comprising a compound according to claim 1, in combination with an excipient.

* * * * *